US009877006B2

(12) United States Patent
Jingu et al.

(10) Patent No.: US 9,877,006 B2
(45) Date of Patent: Jan. 23, 2018

(54) IMAGE PICKUP APPARATUS AND METHOD FOR OPERATING IMAGE PICKUP APPARATUS

(71) Applicant: OLYMPUS CORPORATION, Tokyo (JP)

(72) Inventors: Kazuyoshi Jingu, Inagi (JP); Kenji Omachi, Hachioji (JP); Hiroyuki Nagamizu, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/389,996

(22) Filed: Dec. 23, 2016

(65) Prior Publication Data

US 2017/0111624 A1    Apr. 20, 2017

Related U.S. Application Data

(63) Continuation of application No. PCT/JP2015/083873, filed on Dec. 2, 2015.

(30) Foreign Application Priority Data

Feb. 26, 2015   (JP) ................. 2015-037151

(51) Int. Cl.
*A61B 1/06* (2006.01)
*A61B 1/04* (2006.01)
(Continued)

(52) U.S. Cl.
CPC ............ *H04N 9/735* (2013.01); *A61B 1/04* (2013.01); *A61B 1/06* (2013.01); *G02B 23/2484* (2013.01);
(Continued)

(58) Field of Classification Search
CPC ........ A61B 1/04; A61B 1/06; G02B 23/2484; G02B 17/08; H04N 2005/2255;
(Continued)

(56) References Cited

U.S. PATENT DOCUMENTS 3,549,260 A  * 12/1970 Barringer .............. G01J 3/4537
                                              356/454
7,755,748 B2 *  7/2010 Arnz ..................... G03F 7/70591
                                              356/124
(Continued)

FOREIGN PATENT DOCUMENTS

| JP | 2007-318533 A | 12/2007 |
| JP | 2008-236635 A | 10/2008 |
| JP | 2010-035131 A | 2/2010 |

OTHER PUBLICATIONS

International Search Report dated Feb. 23, 2016 issued in PCT/JP2015/083873.

*Primary Examiner* — Gims Philippe
(74) *Attorney, Agent, or Firm* — Scully, Scott, Murphy & Presser, P.C.

(57) ABSTRACT

An image pickup apparatus is an image pickup apparatus capable of acquiring an image of an object in gas and in liquid, the image pickup apparatus including: an image pickup optical system; an image pickup device; a controlling portion configured to make an in-gas judgment if a vignetting portion is detected in an image signal and make an in-liquid judgment if a vignetting portion is not detected in the image signal; and a display data generating portion configured to generate certain display data corresponding to in-gas image pickup if the in-gas judgment is made and generate other display data corresponding to in-liquid image pickup if the in-liquid judgment is made.

7 Claims, 8 Drawing Sheets

(51) Int. Cl.
  *H04N 9/73*    (2006.01)
  *H04N 5/225*   (2006.01)
  *H04N 5/232*   (2006.01)
  *G02B 23/24*   (2006.01)
  *G03B 17/08*   (2006.01)
  *H04N 5/235*   (2006.01)

(52) U.S. Cl.
  CPC ............ *G03B 17/08* (2013.01); *H04N 5/225* (2013.01); *H04N 5/232* (2013.01); *H04N 5/2354* (2013.01); *H04N 2005/2255* (2013.01)

(58) Field of Classification Search
  CPC ...... H04N 5/225; H04N 5/232; H04N 5/2354; H04N 9/735
  USPC .......................................................... 348/68
  See application file for complete search history.

(56) References Cited

U.S. PATENT DOCUMENTS

| | | | | |
|---|---|---|---|---|
| 8,038,606 B2 * | 10/2011 | Otawara | ............ | A61B 1/00091 600/129 |
| 2008/0231696 A1 | 9/2008 | Kodama et al. | | |
| 2015/0312483 A1 * | 10/2015 | Hikita | ....................... | G06T 3/40 600/109 |

\* cited by examiner

IMAGE PICKUP APPARATUS AND METHOD FOR OPERATING IMAGE PICKUP APPARATUS

CROSS REFERENCE TO RELATED APPLICATION

This application is a continuation application of PCT/JP2015/083873 filed on Dec. 2, 2015 and claims benefit of Japanese Application No. 2015-037151 filed in Japan on Feb. 26, 2015, the entire contents of which are incorporated herein by this reference.

BACKGROUND OF INVENTION

1. Field of the Invention

The present invention relates to an image pickup apparatus capable of acquiring an image of an object in gas and liquid, and a method for operating the image pickup apparatus.

2. Description of the Related Art

Some image pickup apparatuses not only pick up an image of an object existing in gas such as air but also pick up an image of an object existing in liquid such as water.

For example, in Japanese Patent Application Laid-Open Publication No. 2007-318533, a digital camera capable of performing stroboscopic photographing in water by being accommodated in a waterproof pack is described. However, a lens portion is configured larger in a case of a waterproof pack of a lens projection type digital camera, and, therefore, when stroboscopic photographing is performed with a built-in strobe, strobe light is blocked by the lens portion, and vignetting occurs. Therefore, Japanese Patent Application Laid-Open Publication No. 2007-318533 proposes a technique in which whether an underwater photographing mode is set or not, and, if it is judged that the underwater photographing mode is set, image processing for correcting an image where vignetting by strobe light has occurred to an image without the vignetting is performed.

Further, in Japanese Patent Application Laid-Open Publication No. 2010-35131, a technique is described in which, when a conversion lens is fitted to a digital camera, vignetting caused by the conversion lens is detected. More specifically, in Japanese Patent Application Laid-Open Publication No. 2010-35131, image data is separated longitudinally and laterally to divide the image data into areas with an appropriate size; an exposure value in each area is measured to calculate an evaluation value; and it is detected that vignetting has occurred in the image data if such an evaluation value pattern that evaluation values around the image data are values indicating black is detected.

SUMMARY OF THE INVENTION

An image pickup apparatus according to a certain aspect of the present invention is an image pickup apparatus capable of acquiring an image of an object in gas and in liquid, the image pickup apparatus including: an image pickup optical system configured to form an optical image of the object; an image pickup device configured to photoelectrically convert the optical image to generate an image signal; a judging portion configured to make an in-gas judgment indicating that the image signal is acquired in gas if a vignetting portion is detected in the image signal and make an in-liquid judgment indicating that the image signal is acquired in liquid if a vignetting portion is not detected in the image signal; and a display data generating portion configured to generate display data corresponding to in-gas image pickup if the in-gas judgment is made and generate display data corresponding to in-liquid image pickup different from the display data corresponding to the in-gas image pickup if the in-liquid judgment is made.

A method for operating an image pickup apparatus according to a certain aspect of the present invention is a method for operating an image pickup apparatus capable of acquiring an image of an object in gas and in liquid, the method including steps of: an image pickup optical system forming an optical image of the object; an image pickup device photoelectrically converting the optical image to generate an image signal; a judging portion making an in-gas judgment indicating that the image signal is acquired in gas if a vignetting portion is detected in the image signal and making an in-liquid judgment indicating that the image signal is acquired in liquid if a vignetting portion is not detected in the image signal; and a display data generating portion generating display data corresponding to in-gas image pickup if the in-gas judgment is made and generating display data corresponding to in-liquid image pickup different from the display data corresponding to the in-gas image pickup if the in-liquid judgment is made.

DETAILED DESCRIPTION OF THE PREFERRED EMBODIMENT(S)

An embodiment of the present invention will be described below with reference to drawings.

[First Embodiment]

Figure 1:
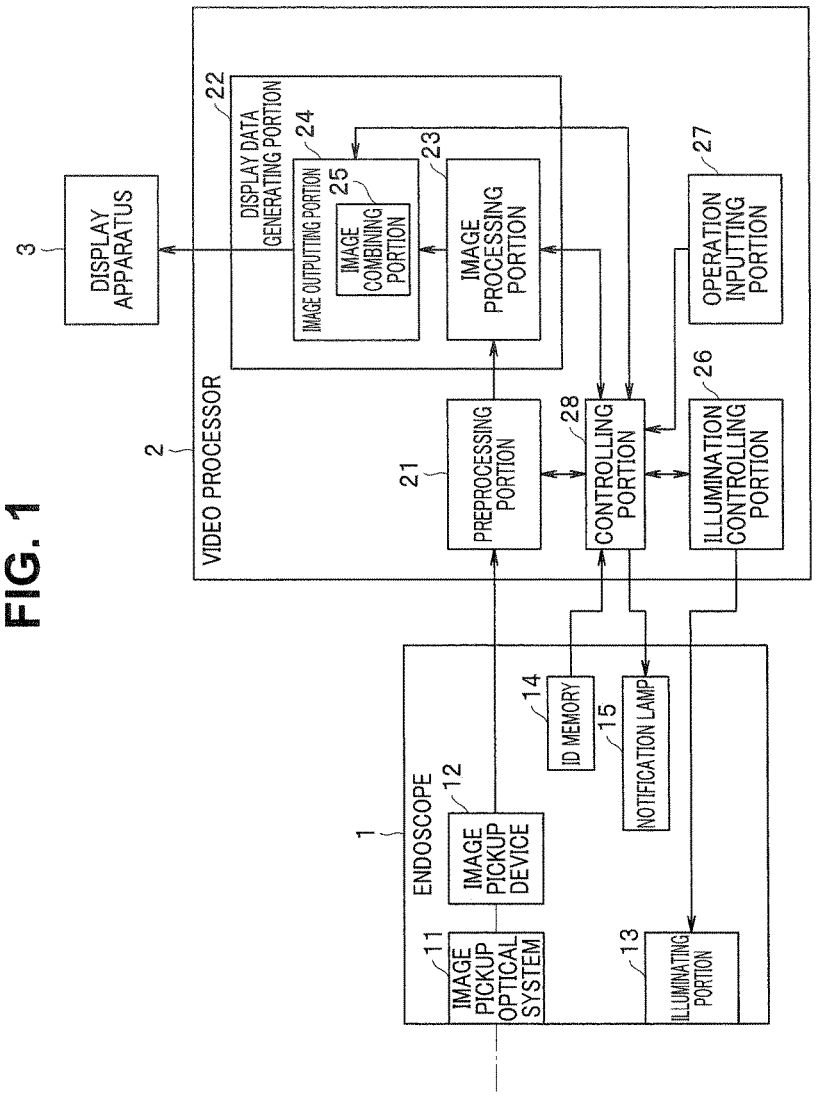
FIG. 1 is a block diagram showing a configuration of an endoscope system in a first embodiment of the present invention.

FIGS. 1 to 11 show a first embodiment of the present invention, and FIG. 1 is a block diagram showing a configuration of an endoscope system. That is, the present embodiment is an embodiment in which an image pickup apparatus is applied to an endoscope system.

The endoscope system is provided with an endoscope 1, a video processor 2 and a display apparatus 3.

The endoscope 1 is capable of acquiring an image of an object in gas as well as in liquid, and is provided with an image pickup optical system 11, an image pickup device 12, an illuminating portion 13, an ID memory 14 and a notification lamp 15.

The image pickup optical system 11 is an optical system configured to form an optical image of an object from light incident via gas or liquid existing on an object side.

The image pickup device 12 is an image pickup portion configured to photoelectrically convert the optical image formed by the image pickup optical system 11 to generate an image signal.

Figure 5:
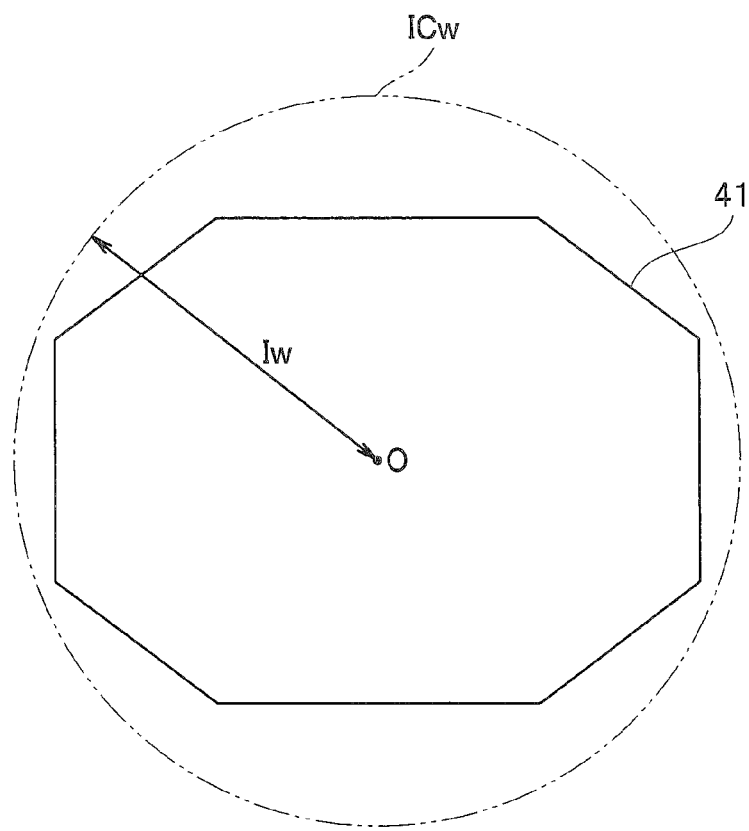
FIG. 5 is a diagram showing an example of an endoscope image obtained by in-liquid image pickup, which is displayed on a screen of a display apparatus, in the above first embodiment.

The image pickup optical system 11 described above is designed so that, in a case of forming an optical image of an object in liquid, an image pickup surface of the image pickup device 12 is within an image circle ICw (see FIG. 5 and the like). However, the image pickup optical system 11 is in such a configuration that, in a case of the image pickup optical system 11 forming an optical image of an object in gas, an image circle ICa (see FIG. 6 and the like) becomes smaller, and a vignetting portion VP, which is outside the image circle ICa, occurs within the image pickup surface of the image pickup device 12 (see examples shown in FIGS. 7 and 8 also).

Figure 3:
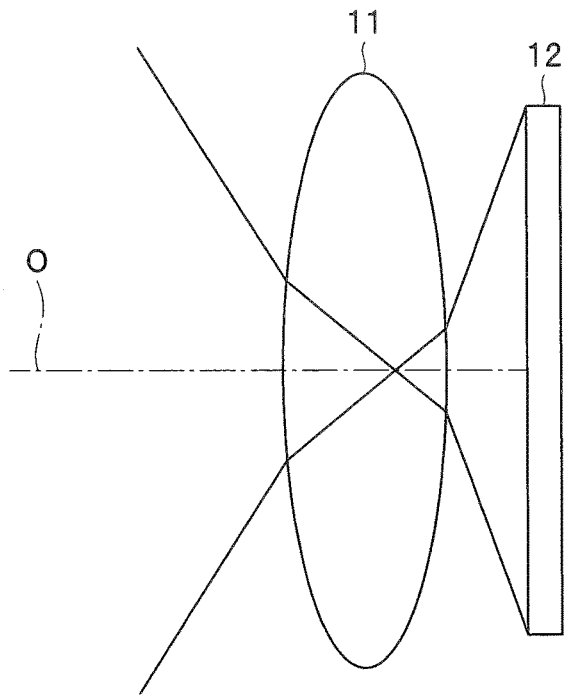
FIG. 3 is a diagram showing an example of an optical path of light which is image-formed on an image pickup device by an image pickup optical system an object side of which is positioned in liquid, in the above first embodiment.
Figure 4:
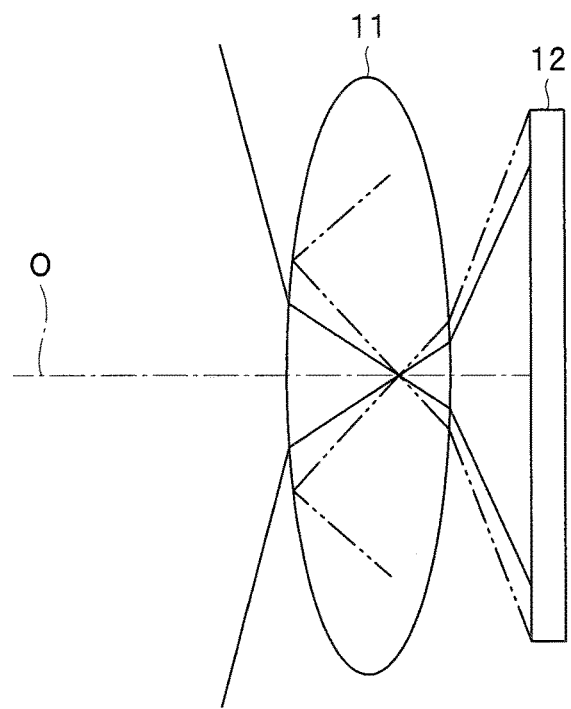
FIG. 4 is a diagram showing an example of an optical path of light which is image-formed on the image pickup device by the image pickup optical system the object side of which is positioned in gas, in the above first embodiment.

Here, a reason why the vignetting portion VP occurs in gas will be described with reference to FIGS. 3 and 4. FIG. 3 is a diagram showing an example of an optical path of light which is image-formed on the image pickup device 12 by the image pickup optical system 11 an object side of which is positioned in liquid. FIG. 4 is a diagram showing an example of an optical path of light which is image-formed on the image pickup device 12 by the image pickup optical system 11 the object side of which is positioned in gas.

If the gas is air, a refractive index is about 1.00. If the liquid is water, a refractive index is about 1.33. In comparison, a refractive index of glass material forming the image pickup optical system 11 is generally higher than the refractive indexes of air and water and is, for example, about 1.43 to 2.14.

Therefore, an image-pickup angle of view in gas as shown in FIG. 4 is generally wider than an image-pickup angle of view in liquid as shown in FIG. 3. At this time, when it is attempted to realize a wider angle of view in liquid, an angle of view in gas which is theoretically calculated from the refractive index may exceed a maximum angle range within which light can be incident, due to a shape of an incident surface of the image pickup optical system 11 (for example, if the incident surface is flat, the maximum angle range within which light can be incident is 180°). Actually, there is no incidence of light from an angle-of-view range exceeding the maximum angle range. Therefore, at this time, if light which reaches an edge of the image pickup surface of the image pickup device 12 is reverse-traced, a state that total reflection occurs on an inner face side of the incident surface of the image pickup optical system 11 is obtained, as shown by a two-dot chain line in FIG. 4. Vignetting which occurs at an edge of an image picked up in such a state will be referred to, for example, as "total reflection vignetting" in the present specification.

When such total reflection vignetting occurs, a vignetting portion, which is not an effective image, occurs around an effective image area, and an inner surface of a lens frame of the image pickup optical system 11 may be displayed in the vignetting portion due to the total reflection vignetting in the inner surface described above. When such display is observed on the display apparatus 3, a user may misrecognize that a fault has occurred or may be given unnatural feeling from the display.

Figure 6:
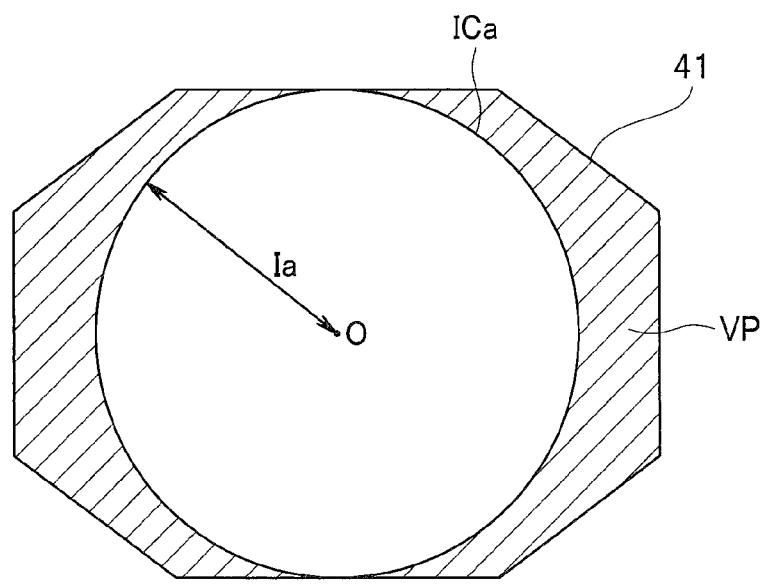
FIG. 6 is a diagram showing an example of an endoscope image obtained by in-gas image pickup, which is displayed on the screen of the display apparatus, in the above first embodiment.

FIG. 5 is a diagram showing an example of an endoscope image 41 obtained by in-liquid image pickup, which is displayed on a screen of the display apparatus 3; and FIG. 6 is a diagram showing an example of an endoscope image 41 obtained by in-gas image pickup, which is displayed on the screen of the display apparatus 3.

In the case of in-liquid image pickup, since the image circle ICw (note that a character w is attached in order to show that the image circle IC is in liquid) includes the endoscope image 41 inside, a vignetting portion does not occur, as shown in FIG. 5.

In comparison, in the case of in-gas image pickup shown in FIG. 6, an image circle ICa (note that a character a is attached in order to show that the image circle IC is in gas) with a radius Ia smaller than a radius Iw of the image circle ICw in liquid shown in FIG. 5, with an optical axis O as a center, is obtained, and, further, the image circle ICa cannot cover a whole area of the endoscope image 41. Therefore, a vignetting portion VP indicated by hatching occurs on an edge portion of the endoscope image 41.

In the example shown in FIG. 6, the diameter of the image circle IC is same as a length of a short side of the endoscope image 41. According to a configuration of the image pickup optical system 11, however, there may be a case where the diameter of the image circle IC is smaller than the short side of the endoscope image 41 or a case where the diameter of the image circle IC is of a length between the short side and long side of the endoscope image 41. Examples of the above are shown in FIGS. 7 and 8.

Figure 7:
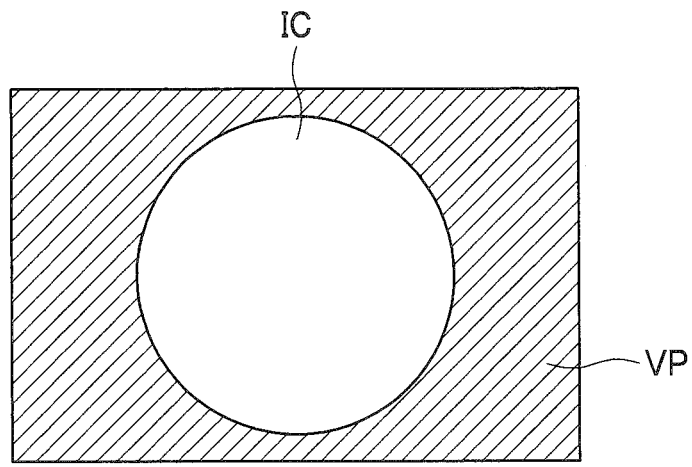
FIG. 7 is a diagram showing an example of an image obtained by in-gas image pickup in the above first embodiment.

First, FIG. 7 is a diagram showing an example of an image obtained by in-gas image pickup.

In the example shown in FIG. 7, the diameter of the image circle IC is smaller than the short side of the image pickup surface of the image pickup device 12, and an image of the image circle IC is formed in a circular shape on the image pickup device 12, so that an outside portion of the image circle IC is a vignetting portion VP caused by the total reflection vignetting described above.

Figure 8:
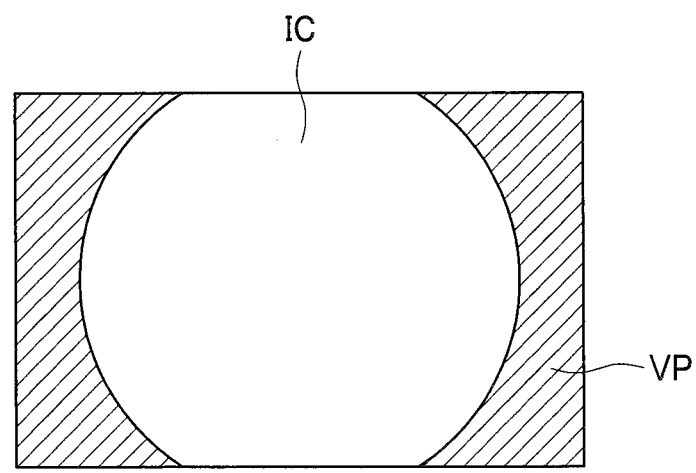
FIG. 8 is a diagram showing another example of an image obtained by in-gas image pickup in the above first embodiment.

Further, FIG. 8 is a diagram showing another example of an image obtained by in-gas image pickup.

In the example shown in FIG. 8, the diameter of the image circle IC is larger than the short side of the image pickup surface of the image pickup device 12 and smaller than a long side; and an outline of an image of the image circle IC is in a circular shape, and left and right outside portions of the image circle IC are vignetting portions VP caused by the total reflection vignetting described above.

Returning to the description of FIG. 1, the illuminating portion 13 radiates illuminating light to an object and is configured including a light-emitting device such as an LED, a light guide fiber configured to transmit the illuminating light, or the like.

The ID memory 14 is a storage portion configured to nonvolatilely store an endoscope ID. More specifically, information such as a model number and a serial number of the endoscope 1 is stored. It is possible to identify, for example, based on information about the model number of the endoscope 1 among the pieces of information, that the endoscope 1 is an endoscope of a type capable of acquiring an image signal both in gas and in liquid. Furthermore, if the endoscope 1 is an endoscope of the type capable of acquiring an image signal both in gas and in liquid, a controlling portion 28 to be described later can acquire outline information such as a position and size of the image circle IC based on the information about the model number of the endoscope 1, by referring to a database or the like. Otherwise, the outline information such as the position and size of the image circle IC is stored in the ID memory 14 in advance, and the information is read by the controlling portion 28.

The notification lamp 15 is provided, for example, on an operation portion of the endoscope 1, and the notification lamp 15 is a notification portion configured to, when an in-gas judgment indicating that an image signal has been obtained by in-gas image pickup or an in-liquid judgment indicating that an image signal has been obtained by in-liquid image pickup is made by the controlling portion 28 in the video processor 2, which is to be described later, notify the user of the judgment result by lighting/extinction of the lamp. Here, as an example, a configuration is made so that the notification lamp 15 is turned on when the in-liquid judgment is made, and the notification lamp 15 is turned off when the in-gas judgment is made.

Note that, though an example has been described in which the notification lamp 15 is provided on the operation portion of the endoscope 1, the notification lamp 15 is not limited to the arrangement but may be provided on an exterior of the video processor 2 or may be provided on the display apparatus 3. (Here, though it is possible to perform notification display on the screen of the display apparatus 3 as described later with reference to FIG. 10, it is recommended to provide the notification lamp 15 on an exterior of the display apparatus 3, for example, in a case of displaying an endoscope image on the whole screen of the display apparatus 3.)

The video processor 2 is provided with a preprocessing portion 21, a display data generating portion 22, an illumination controlling portion 26, an operation inputting portion 27 and the controlling portion 28.

The preprocessing portion 21 performs, for example, a process for amplifying an image signal inputted from the image pickup device 12 and converting the image signal to a digital signal.

The display data generating portion 22 generates display data by performing image processing for the image signal inputted from the preprocessing portion 21 and is provided with an image processing portion 23 and an image outputting portion 24. If an in-gas judgment is made by the controlling portion 28 to be described later, the display data generating portion 22 generates display data corresponding to in-gas image pickup from the image signal. If an in-liquid judgment is made, the display data generating portion 22 generates display data corresponding to in-liquid image pickup which is different from the display data corresponding to in-gas image pickup from the image signal.

Figure 2:
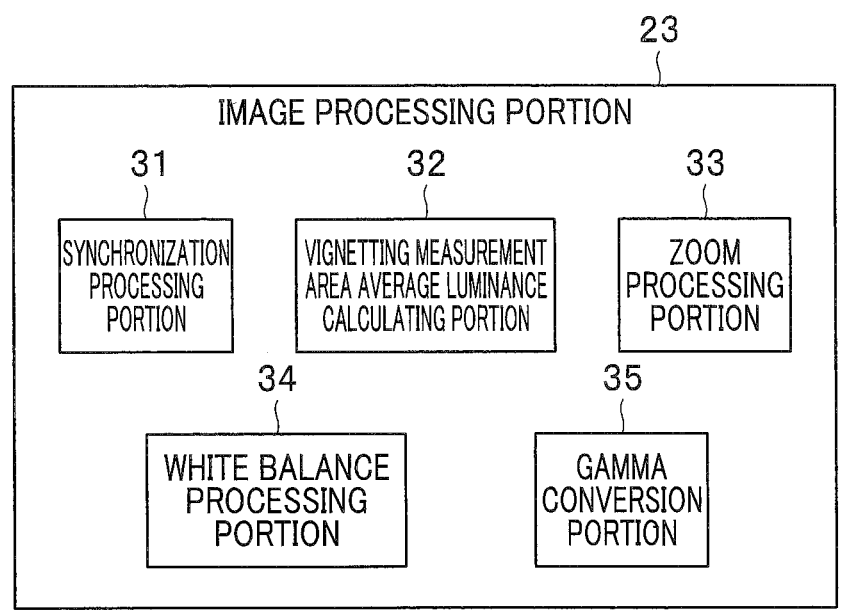
FIG. 2 is a block diagram showing a configuration of an image processing portion in the above first embodiment.

Here, FIG. 2 is a block diagram showing a configuration of the image processing portion 23.

The image processing portion 23 is provided with a synchronization processing portion 31, a vignetting measurement area average luminance calculating portion 32, a zoom processing portion 33, a white balance processing portion 34 and a gamma conversion portion 35.

For example, when the image pickup device 12 is a monochrome image pickup device, and a color image signal is acquired by frame sequential illumination, the synchronization processing portion 31 performs synchronization processing of acquired images of respective colors to create one color image. Further, when the image pickup device 12 is a single-plate color image pickup device provided with a primary color Bayer array color filter, for example, the synchronization processing portion 31 performs demosaicking processing of an acquired Bayer image to create one color image.

The vignetting measurement area average luminance calculating portion 32 sets a whole or a part of the vignetting portion VP outside the image circle IC which occurs when the endoscope 1 acquires an image signal in gas as a vignetting measurement area (the vignetting measurement area does not become a vignetting portion VP when the endoscope 1 acquires an image signal in liquid, as described above) in advance and calculates, for example, average luminance of the vignetting measurement area.

Note that, in both of the examples shown in FIGS. 7 and 8 described above, left and right edge portions (both edge portions in a long side direction) of the image are vignetting portions VP similarly. Therefore, by limiting the vignetting measurement area to be described later to the left and right edge portions outside the IC image circle, it becomes possible to use vignetting measurement areas common to a plurality of kinds of endoscopes, and it is possible to uniform processing. Otherwise, more limitatively, four corner portions in upper, lower, left and right of an image may be caused to be the vignetting measurement areas.

Further, though the average luminance is calculated here, the method is not limited to this. A median of luminance distribution of the vignetting measurement areas, a peak value of appearance frequency of luminance, and the like may be used. In short, any value representing luminances of the vignetting measurement areas is possible.

The controlling portion 28 functions as a judging portion configured to compare the average luminance of the vignetting measurement areas calculated by the vignetting measurement area average luminance calculating portion 32 with a predetermined threshold, and judges that a vignetting portion VP is not detected, that is, image pickup has been performed in liquid if the average luminance is equal to or above the threshold, and that a vignetting portion VP is detected, that is, image pickup has been performed in gas if the average luminance is below the threshold.

The zoom processing portion 33 performs electronic zoom processing of cutting out and enlarging a part of an image acquired from the image pickup device 12. The zoom processing portion 33 performs electronic zoom processing corresponding to setting content when a manual zoom operation is performed. Further, in the present embodiment, when an automatic zoom mode is set, and an in-gas judgment is made, the zoom processing portion 33 performs automatic processing for generating display data by cutting out and enlarging an image portion in the image circle IC except a vignetting portion VP, in an image signal acquired by in-gas image pickup.

Figure 9:
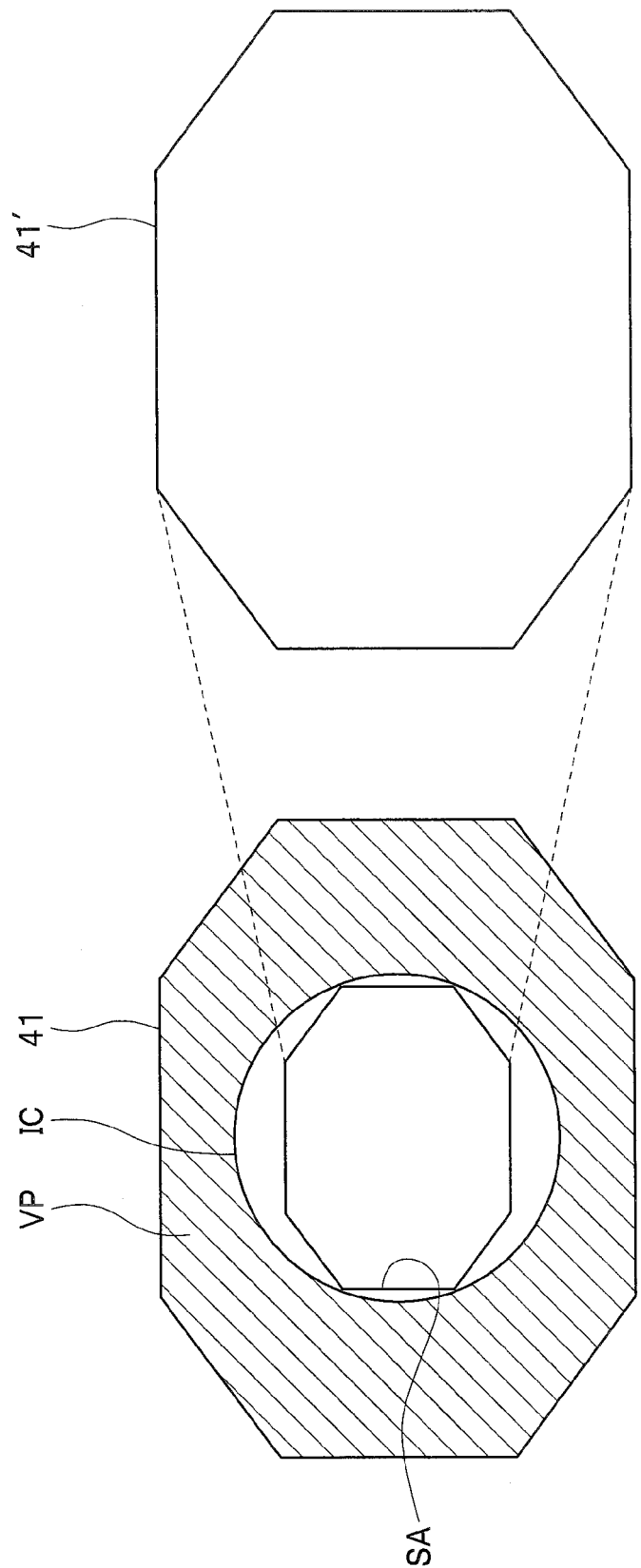
FIG. 9 is a diagram showing a state that an image signal acquired in gas is zoom-processed in the above first embodiment.

FIG. 9 is a diagram showing a state that an image signal acquired in gas is zoom-processed.

An endoscope image 41 obtained by processing an image signal acquired in gas includes an effective image area inside the image circle IC and a vignetting portion VP outside the image circle IC as described above. Therefore, if it is judged by the controlling portion 28 that an image signal has been generated by in-gas image pickup, the zoom processing portion 33 generates a new endoscope image 41' as display data by cutting out and enlarging an image portion SA inside the image circle IC in the image signal.

Note that, at time of performing the automatic zoom processing, it is preferable to set an enlargement ratio so that a same object that is image-picked up in liquid is displayed on the display apparatus 3 with an almost same size at the time of in-gas image pickup also, because unnatural feeling given when switching is performed between in-liquid image pickup and in-gas image pickup is reduced.

The white balance processing portion 34 measures white balance based on an image signal obtained from the image pickup device 12 and performs white balance adjustment on the image signal based on a measurement result. If the image signal is configured, for example, with three components of RGB, the white balance processing portion 34 performs white balance adjustment by multiplying the R, G and B components by respective gains so that a white object is observed in white.

The white balance processing portion 34 is adapted to, at this time, set a whole or a part of the image signal obtained from the image pickup device 12 as a white balance measurement range if the judgment result by the controlling portion 28 is an in-liquid judgment, and set a whole or a part of a portion excluding a vignetting portion VP (the effective image area inside the image circle IC) in the image signal obtained from the image pickup device 12 as the white balance measurement range if the judgment result is an in-gas judgment.

The gamma conversion portion 35 performs gradation conversion so that gradation characteristics of an image signal become suitable for display characteristics of the display apparatus 3.

The image outputting portion 24 generates display data to be displayed on the display apparatus 3 from an image signal processed by the image processing portion 23 and includes an image combining portion 25.

Here, the image combining portion 25 performs image combination for superimposing notification display data for notifying the judgment result by the controlling portion 28 on the display data.

Figure 10:
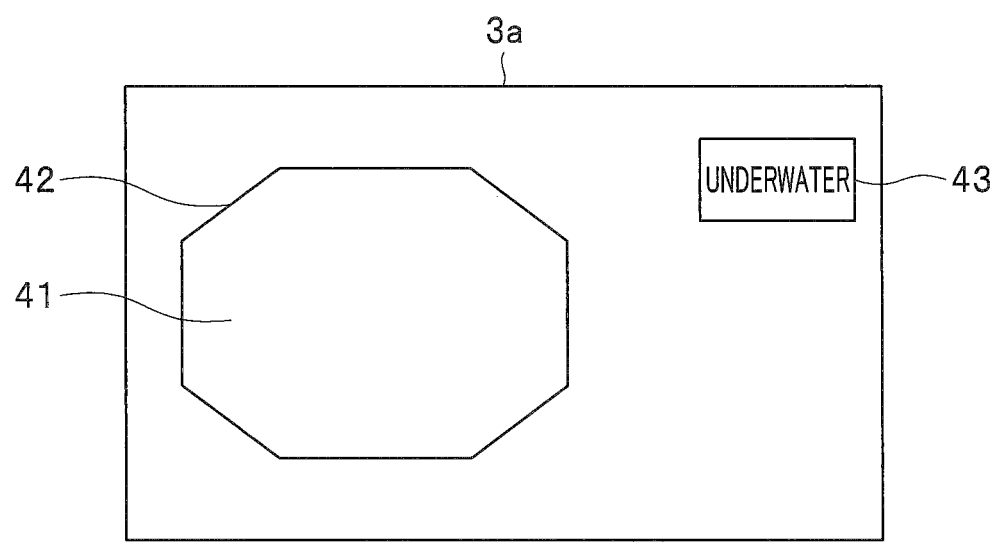
FIG. 10 is a diagram showing an example of notification display data displayed on the display apparatus of the above first embodiment.

FIG. 10 is a diagram showing an example of the notification display data displayed on the display apparatus 3.

A display screen 3a of the display apparatus 3 is adapted so that an image acquired by the endoscope 1 is displayed as an endoscope image 41.

An example of the notification display is such that a display aspect of a frame line 42 surrounding the endoscope image 41 is caused to differ in a case where the endoscope image 41 has been acquired in liquid and a case where the endoscope image 41 has been acquired in gas. As some examples of specific difference of the display aspect, it is conceivable to cause a thickness of the frame line 42 to differ, cause a color to differ, cause a line type (single line, double line, dotted line, one-dot chain line, two-dot chain line and the like) to differ, and so on.

Further, another example of the notification display is to display an image pickup environment display 43 such as characters and a mark indicating whether the endoscope image 41 has been acquired in liquid or in gas.

Only one of the frame line 42 and the image pickup environment display 43 may be displayed, or both of the frame line 42 and the image pickup environment display 43 may be simultaneously displayed. Further, the notification display is not limited to the above examples, but other notification displays are also possible. The notification by the notification lamp 15 described above may be used together with the above notification displays, or only one of the notification displays may be used.

The illumination controlling portion 26 performs photometry based on an image signal obtained from the image pickup device 12 and controls, for example, an amount (or, additionally directivity and the like) of illuminating light radiated by the illuminating portion 13 to an object based on the measurement result. That is, the illumination controlling portion 26 controls the illuminating portion 13 to cause the amount of illuminating light to decrease if brightness of an image is larger than a proper value and controls the illuminating portion 13 to cause the amount of illuminating light to increase if the brightness of the image is smaller than the proper value.

The illumination controlling portion 26 is adapted to, at this time, change a photometry range based on an in-gas judgment result or an in-liquid judgment result by the controlling portion 28. That is, the illumination controlling portion 26 is adapted to set a whole or a part of an image signal obtained from the image pickup device 12 as the photometry range if the judgment result by the controlling portion 28 is an in-liquid judgment, and set a whole or a part of a portion excluding a vignetting portion VP (the effective image area inside the image circle IC) in the image signal obtained from the image pickup device 12 as the photometry range if the judgment result is an in-gas judgment.

The operation inputting portion 27 performs an operation input to the endoscope system including the video processor 2, and is configured, appropriately including an operation switch, an operation panel, a keyboard and a mouse, a trackball and the like. Note that, though the example shown in FIG. 1 shows an example in which the operation inputting portion 27 is provided on the video processor 2, an operation switch or the like provided on the endoscope 1 is also possible, or an external operation inputting portion, such as a foot switch, is also possible. Arrangement is not limited to these. For the operation inputting portion 27 of the present embodiment, the automatic zoom mode for automatically cutting out and zoom-enlarging an image inside the image circle IC in an image signal acquired in gas can be set. Further, it is possible to perform manual zoom by the operation inputting portion 27.

The controlling portion 28 comprehensively controls the whole endoscope system including the video processor 2.

For example, the controlling portion 28 acquires an endoscope ID from the ID memory 14 described above and performs a process corresponding to the acquired endoscope LD, that is, processing corresponding to a kind and the like of a connected endoscope 1. More specifically, if identifying that the endoscope 1 is an endoscope of the type capable of acquiring an image signal both in gas and in liquid, the controlling portion 28 performs a process to be described later with reference to FIG. 11 and the like.

Further, the controlling portion 28 functions as the judging portion as described above. For example, based on average luminance of a vignetting measurement area calculated by the vignetting measurement area average luminance calculating portion 32, the controlling portion 28 makes an in-gas judgment indicating that an image signal has been acquired in gas if a vignetting portion VP (a portion outside the image circle IC) is detected in the image signal, and makes an in-liquid judgment indicating that the image signal has been acquired in liquid if a vignetting portion VP is not detected in the image signal.

The display apparatus 3 is a display portion configured to display, for example, the endoscope image 41, the notification display data and the like as shown in FIG. 10 by display data generated by the video processor 2.

Figure 11:
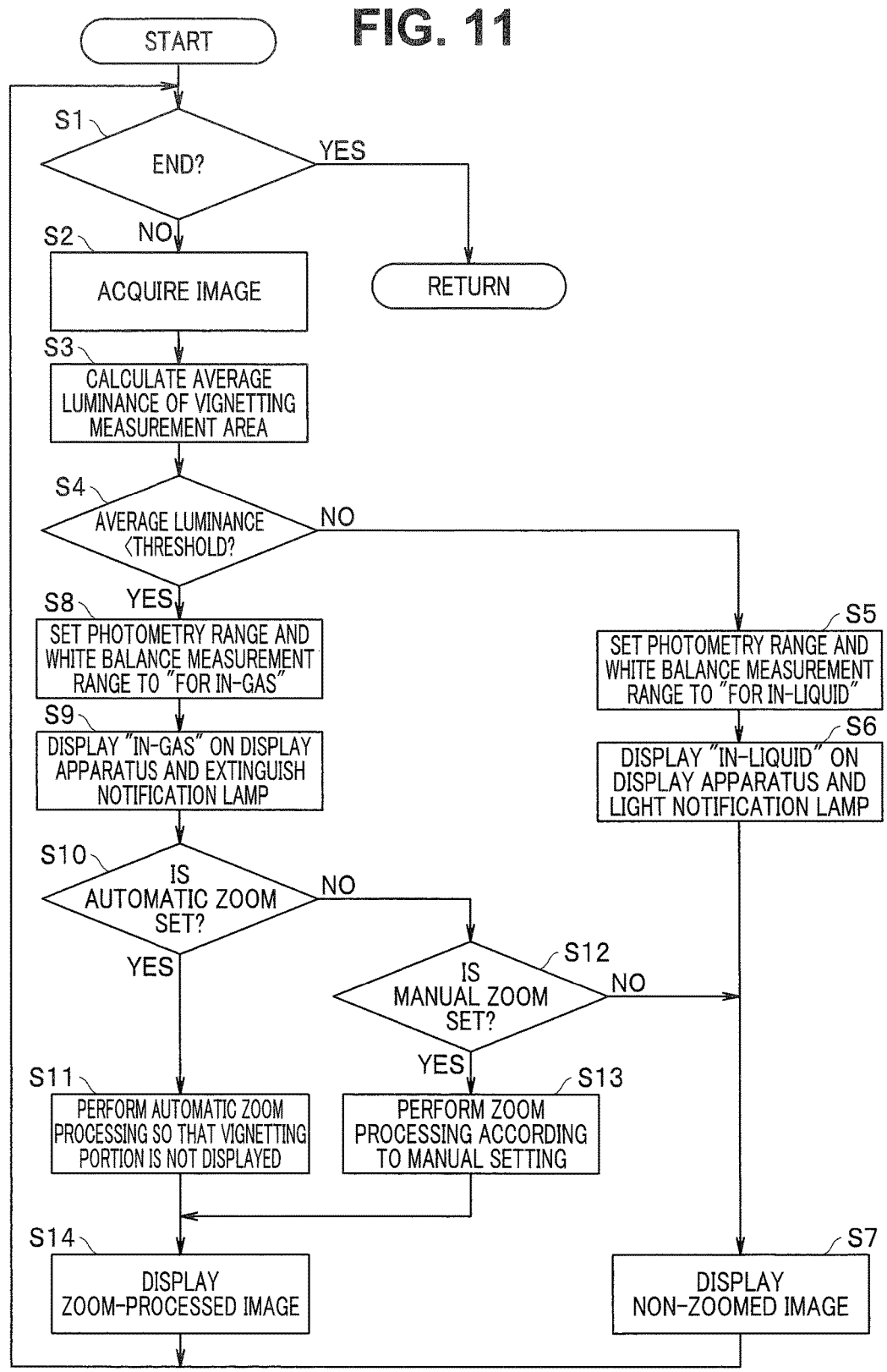
FIG. 11 is a flowchart showing operation of an image pickup apparatus in the above first embodiment.

FIG. 11 is a flowchart showing operation of the image pickup apparatus. When the process is started, it is judged whether or not to end the process (step S1). If the process is not to be ended, image pickup is performed by the image pickup device 12 to acquire an image signal (step S2). The acquired image signal is inputted to the image processing portion 23 after being processed by the preprocessing portion 21.

The image processing portion 23 performs a synchronization process for the inputted image signal by the synchronization processing portion 31 and, after that, calculates average luminance of a vignetting measurement area by the vignetting measurement area average luminance calculating portion 32 (step S3).

The controlling portion 28 acquires the calculated average luminance of the vignetting measurement area and compares the average luminance with a predetermined threshold (step S4).

If it is judged at step S4 that the average luminance is equal to or above the threshold (that is, if an in-liquid judgment is made), the controlling portion 28 controls the illumination controlling portion 26 to set the photometry range to an in-liquid photometry range and controls the white balance processing portion 34 to set the white balance measurement range to an in-liquid white balance measurement range (step SS).

Furthermore, by controlling the image combining portion 25 to superimpose notification display data corresponding to in-liquid image pickup on display data, the controlling portion 28 causes the frame line 42 and the image pickup environment display 43 as shown in FIG. 10 to be displayed on the display apparatus 3 and causes the notification lamp 15 to be turned on to notify that in-liquid image pickup has been performed (step S6).

After that, a non-zoomed image acquired from the image pickup device 12 is displayed on the display apparatus 3 without being zoom-processed by the zoom processing portion 33 (step S7).

On the other hand, if it is judged at step S4 that the average luminance is below the threshold (that is, if an in-gas judgment is made), the controlling portion 28 controls the illumination controlling portion 26 to set the photometry range to the in-gas photometry range and control the white balance processing portion 34 to set the white balance measurement range to the in-gas white balance measurement range (step S8).

Furthermore, by controlling the image combining portion 25 to superimpose notification display data corresponding to in-gas image pickup on the display data, the controlling portion 28 causes the frame line 42 and the image pickup environment display 43 as shown in FIG. 10 to be displayed on the display apparatus 3 and causes the notification lamp 15 to be turned off to notify that in-gas image pickup has been performed (step S9).

After that, the controlling portion 28 judges whether or not the automatic zoom mode is set (step S10).

Here, if it is judged that the automatic zoom mode is set, the zoom processing portion 33 performs zoom processing so that a vignetting portion VP is not displayed, and cuts out and enlarges the image portion SA inside the image circle IC as shown in FIG. 9 to generate a display image (step S11).

Further, if it is judged at step S10 that the automatic zoom mode is not set, it is judged whether a manual zoom operation has been performed from the operation inputting portion 27 to set zooming (step S12).

If it is judged that manual zoom setting has not been made here, the flow goes to step S7 described above, and a non-zoomed image is displayed on the display apparatus 3.

In comparison, if it is judged that the manual zoom setting has been made, the zoom processing portion 33 performs zoom processing and generates a display image with a zoom magnification corresponding to the manual setting (step S13).

When a zoom-processed display image is generated by step S11 or step S13, the generated zoomed image is displayed on the display apparatus 3 (step S14).

When the processing of step S7 or step S14 are performed, the flow returns to step S1 and judges whether or not to end the process as described above. By performing such a loop process, the judgment of comparison between average luminance and the threshold by step S4, that is, a judgment about whether image pickup is in-liquid image pickup or in-gas image pickup is periodically made in a constant cycle.

Then, if it is judged at step S1 that the process is to be ended, the flow returns from the process to a main process not shown.

Note that, though a value representing luminances of the vignetting measurement area (for example, average luminance) is calculated and compared with a predetermined threshold to judge whether the image pickup is in-gas image pickup or in-liquid image pickup in the above description, other judgment methods may be used.

For example, a first modification of the judgment method is a method of determining luminance difference between a vignetting measurement area and an effective image area included inside the image circle IC. For example, suppose that a plurality of luminance measurement points are set in the vignetting portion VP as shown in FIG. 7 or 8, more specifically, the luminance measurement points are set, for example, at four corners of the vignetting portion VP, and that luminances measured at the four luminance measurement points are L1 to L4. Furthermore, suppose that a luminance measurement point is also set, for example, at a center of the image circle IC as shown in FIG. 7 or 8, and that luminance measured at the luminance measurement point is L0. At this time, a following discrimination value D which gives the luminance difference between the vignetting measurement area and the effective image area is calculated.

$$D=L0-(L1+L2+L3+L4)/4$$

Then, the calculated discrimination value D is compared with a threshold Th determined in advance. If the discrimination value D is smaller than the threshold Th (D<Th), it is judged that in-liquid image pickup has been performed. If the discrimination value D is equal to or larger than the threshold Th (D≥Th), it is judged that in-gas image pickup has been performed.

Further, for example, a second modification of the judgment method is a method of detecting an outline of the image circle IC. At which position on the image pickup device 12 the outline of the image circle IC is to be formed is determined in advance according to the configuration of the image pickup optical system 11. Therefore, the controlling portion 28 acquires information about the image pickup optical system 11 (outline information such as the position and size of the image circle IC) from the ID memory 14 (or a database or the like) as described above and performs edge detection in a vicinity of the acquired outline position. As a result, if an edge corresponding to the outline of the image circle IC is detected, it is judged that in-gas image pickup has been performed; and, if not, it is judged that in-liquid image pickup has been performed.

Note that the judgment based on average luminance or luminance difference and the judgment based on an outline detection result may be combined.

Further, though an example of making a visual notification by display has been described above, sound may be used to notify whether the image pick up is in-liquid image pickup or in-gas image pickup instead or additionally. As a specific example, it is conceivable to sound a notification chime of a certain melody when in-liquid image pickup is switched to in-gas image pickup and sound a notification chime of another melody when in-gas image pickup is switched to in-liquid image pickup, and so on. Further, as an another example, it is also possible to make a notification by voice such as "Switched now to in-water observation" when in-gas image pickup is switched to in-liquid image pickup and make a notification by voice such as "Switched now to in-gas observation" when in-liquid image pickup is switched to in-gas image pickup.

Furthermore, though electronic zoom by the zoom processing portion 33 is given as an example of zoom performed by automatic processing in the case of in-gas image pickup in the description above, the zoom may be performed by optical zoom if the image pickup optical system 11 is a zoom optical system. The same goes for zoom by a manual operation.

According to the first embodiment described above, since an in-gas judgment or an in-liquid judgment is made according to whether or not a vignetting portion VP is detected, and different display data according to a judgment result is generated from an image signal, it is possible to perform such image display which is not misrecognized as a fault having occurred even if a vignetting portion VP which does not occur in in-liquid image pickup occurs by in-gas image pickup.

Further, since whether or not a vignetting portion VP is detected is judged based on a result of comparing average luminance of a vignetting measurement area with a predetermined threshold, it is possible to obtain a stable judgment result by simple calculation.

Similarly, when whether or not a vignetting portion VP is detected is judged based on luminance difference between a vignetting measurement area and an effective image area, it is possible to obtain a practical judgment result by simple calculation.

On the other hand, when whether a vignetting portion VP is detected or not is judged based on a result of detecting an outline of the image circle IC, it is possible to obtain an almost certain detection result though a calculation load for causing an outline detection filter to operate occurs.

When the judgment based on average luminance or luminance difference and the judgment based on an outline detection result are combined, it is possible to make a more accurate judgment.

Furthermore, since display data is generated by cutting out and enlarging the image portion SA in the image circle IC if an in-gas judgment is made, it is possible to observe an image without vignetting and eliminate unnatural feeling due to a vignetting portion in the image.

At this time, when an enlargement ratio is set so that a same object is displayed with an almost same size in the case of in-liquid image pickup and in the case of in-gas image pickup, it is possible to further reduce the unnatural feeling at the time of switching between in-liquid image pickup and in-gas image pickup.

Further, since display data is generated so that notification display data indicating a judgment result is included, it is possible to visually confirm that a fault has not occurred. It becomes possible to grasp whether in-liquid image pickup or in-gas image pickup based on a display aspect of the frame line 42 or display content of the image pickup environment display 43. When a notification lamp is used, almost similar effects can be obtained.

On the other hand, when a notification is made with sound, it is not necessary to turn eyes upon the notification display or the notification lamp, and, therefore, it becomes possible for a user such as an operator to grasp which state is selected between in-liquid image pickup and in-gas image pickup, without shifting his eyes from work he is performing.

Further, since a photometry range is appropriately set according to whether an in-liquid judgment or an in-gas judgment is made (that is, since a vignetting portion VP where an effective image is not obtained is excluded from the photometry range), it becomes possible to observe an image with appropriate brightness irrespective of whether in-liquid image pickup or in-gas image pickup.

In addition, since a white balance measurement range is appropriately set according to whether an in-liquid judgment or an in-gas judgment is made (that is, since a vignetting portion VP where an effective image is not obtained is excluded from the white balance measurement range), it becomes possible to observe an image with appropriate white balance irrespective of whether the image pickup is in-liquid image pickup or in-gas image pickup.

Note that an intended use of the endoscope 1 (or the whole endoscope system) described above is not especially limited, and, for example, the endoscope 1 may be either of a medical endoscope or an industrial endoscope. Further, though an example of applying an image pickup apparatus to an endoscope system has been described above, the present invention is not limited to that. The present invention is applicable to any image pickup apparatus if an image of an object can be acquired in gas and in liquid.

Further, each portion described above may be configured as a circuit. An arbitrary circuit may be implemented as a single circuit or may be implemented as a combination of a plurality of circuits, if the circuit can perform a same function. Furthermore, an arbitrary circuit is not limited to such that is configured as a dedicated circuit for performing an intended function, but a configuration is also possible in which the intended function is performed by causing a general-purpose circuit to execute a processing program.

In the above description, an image pickup apparatus has been mainly described. However, a method for operating the image pickup apparatus to operate as described above is also possible, and a control program for causing a computer to control the image pickup apparatus as described above, a computer-readable non-temporary recording medium in which the control program is recorded, and the like are also possible.

Note that the present invention is not limited to the above embodiment as it is, and the components can be modified and embodied within a range not departing from the spirit of the invention at a stage of practicing the invention. Further, various aspects of the invention can be formed by appropriately combining a plurality of components disclosed in the above embodiment. For example, some components may be deleted from all the components shown in the embodiment. Furthermore, components from different embodiments may be appropriately combined. Thus, various modifications and applications are, of course, possible within the range not departing from the spirit of the invention.

What is claimed is:

1. An image pickup apparatus for acquiring an image of an object in gas and in liquid, the image pickup apparatus comprising:
   an image pickup optical system configured to form an optical image of the object;
   an image pickup device configured to photoelectrically convert the optical image to generate an image signal; and
   a processor comprising hardware, wherein the processor is configured to:
      make an in-gas judgment indicating that the image signal is acquired in gas if a vignetting portion is detected in the image signal;
      make an in-liquid judgment indicating that the image signal is acquired in liquid if the vignetting portion is not detected in the image signal;
      generate display data corresponding to in-gas image pickup if the in-gas judgment is made; and
      generate display data corresponding to in-liquid image pickup different from the display data corresponding to the in-gas image pickup if the in-liquid judgment is made.

2. The image pickup apparatus according to claim 1, wherein the processor is configured to:
   judge that the vignetting portion is detected if average luminance of a vignetting measurement area set in advance for the vignetting portion of the image signal in case that of the image signal is acquired in gas is below a predetermined threshold; and
   judge that the vignetting portion is not detected if the average luminance is equal to or above the predetermined threshold.

3. The image pickup apparatus according to claim 1, wherein, if the in-gas judgment is made, the processor is configured to generate the display data corresponding to the in-gas image pickup by cutting out and enlarging an image portion inside an image circle excluding the vignetting portion in the image signal.

4. The image pickup apparatus according to claim 1, wherein the processor is configured to generate the display data corresponding to the in-gas image pickup and the display data corresponding to the in-liquid image pickup so that notification display data for notifying the in-gas judgment and the in-liquid judgment, respectively, is included.

5. The image pickup apparatus according to claim 1, wherein the processor is configured to:
   perform photometry based on the image signal obtained from the image pickup device and control illuminating light to be radiated to the object based on a photometry result; and
   set a whole or a part of the image signal as a photometry range if a judgment result is the in-liquid judgment; and
   set a whole or a part of a portion excluding the vignetting portion in the image signal as the photometry range if the judgment result is the in-gas judgment.

6. The image pickup apparatus according to claim 1, wherein the processor is configured to:
   measure white balance based on the image signal obtained from the image pickup device;
   perform white balance adjustment of the image signal based on a measurement result;
   set a whole or a part of the image signal as a white balance measurement range if a judgment result is the in-liquid judgment; and
   set a whole or a part of a portion excluding the vignetting portion in the image signal as the white balance measurement range if the judgment result is the in-gas judgment.

7. A method for acquiring an image of an object in gas and in liquid, the method comprising steps of:
   an image pickup optical system forming an optical image of the object;
   an image pickup device photoelectrically converting the optical image to generate an image signal;
   a processor comprising hardware making an in-gas judgment indicating that the image signal is acquired in gas if a vignetting portion is detected in the image signal;
   the processor making an in-liquid judgment indicating that the image signal is acquired in liquid if the vignetting portion is not detected in the image signal;
   the processor generating display data corresponding to in-gas image pickup if the in-gas judgment is made; and
   the processor generating display data corresponding to in-liquid image pickup different from the display data corresponding to the in-gas image pickup if the in-liquid judgment is made.

* * * * *